US00RE35988E

United States Patent [19]

Winston et al.

[11] E Patent Number: Re. 35,988

[45] Reissued Date of Patent: Dec. 8, 1998

[54] STENT CONSTRUCTION OF ROLLED CONFIGURATION

[76] Inventors: Thomas R. Winston, 11100 Manor, Leawood, Kans. 66211; John M. Neet, 1762 E. 700 Rd., Lawrence, Kans. 66049

[21] Appl. No.: 630,696

[22] Filed: Apr. 12, 1996

Related U.S. Patent Documents

Reissue of:

[64] Patent No.: 5,306,294
Issued: Apr. 26, 1994
Appl. No.: 925,959
Filed: Aug. 5, 1992

[51] Int. Cl.[6] ..... A61F 2/06

[52] U.S. Cl. ..... 623/1; 623/12; 606/108; 606/191; 606/195; 606/198

[58] Field of Search ..... 623/1, 12; 606/151, 606/153, 155, 108, 191, 198, 195; 604/104, 281

[56] References Cited

U.S. PATENT DOCUMENTS

| | | |
|---|---|---|
| Re. 34,327 | 7/1993 | Kreamer . |
| 3,657,744 | 4/1972 | Ersek . |
| 3,826,257 | 7/1974 | Buselmeier . |
| 3,991,767 | 11/1976 | Miller, Jr. et al. . |
| 4,140,126 | 2/1979 | Choudhury . |
| 4,503,569 | 3/1985 | Dotter . |
| 4,550,447 | 11/1985 | Seiler, Jr. et al. . |
| 4,562,596 | 1/1986 | Kornberg . |
| 4,577,631 | 3/1986 | Kreamer . |
| 4,617,932 | 10/1986 | Kornberg . |
| 4,665,918 | 5/1987 | Garza et al. . |
| 4,723,549 | 2/1988 | Wholey et al. . |
| 4,732,152 | 3/1988 | Wallsten et al. . |
| 4,733,665 | 3/1988 | Palmaz . |
| 4,740,207 | 4/1988 | Kreamer . |
| 4,753,652 | 6/1988 | Langer et al. . |
| 4,776,337 | 10/1988 | Palmaz . |
| 4,787,899 | 11/1988 | Lazarus . |
| 4,820,298 | 4/1989 | Leveen et al. . |
| 4,875,480 | 10/1989 | Imbert . |
| 4,877,030 | 10/1989 | Beck et al. . |
| 4,969,458 | 11/1990 | Wiktor . |
| 4,990,131 | 2/1991 | Dardik et al. . |
| 5,007,926 | 4/1991 | Derbyshire . |
| 5,015,253 | 5/1991 | MacGregor . |
| 5,019,085 | 5/1991 | Hillstead . |
| 5,026,377 | 6/1991 | Burton et al. . |
| 5,037,377 | 8/1991 | Alonso . |
| 5,041,126 | 8/1991 | Gianturco . |
| 5,059,211 | 10/1991 | Stack et al. . |
| 5,078,720 | 1/1992 | Burton et al. . |
| 5,078,726 | 1/1992 | Kreamer . |
| 5,078,736 | 1/1992 | Behl . |
| 5,084,064 | 1/1992 | Barak et al. . |
| 5,089,006 | 2/1992 | Stiles . |
| 5,100,429 | 3/1992 | Sinofsky et al. . |
| 5,104,399 | 4/1992 | Lazarus . |
| 5,108,416 | 4/1992 | Ryan et al. . |
| 5,108,417 | 4/1992 | Sawyer . |

(List continued on next page.)

FOREIGN PATENT DOCUMENTS

| | | |
|---|---|---|
| 678393 A5 | 9/1991 | Switzerland . |
| WO 91/15254 | 10/1991 | WIPO . |
| WO 91/17789 | 11/1991 | WIPO . |
| WO 92/01425 | 2/1992 | WIPO . |

*Primary Examiner*—Paul B. Prebilic
*Attorney, Agent, or Firm*—Knobbe, Martens, Olson & Bear, LLP

[57] ABSTRACT

A stent for reinforcing a damaged wall in a body passage such as a vascular passage. The stent takes the form of a sheet or metal foil wound tightly around a spool in a multiple layer roll and held in a contracted state by a sheath sleeved around the roll. The spool is inserted into the body passage until the stent is adjacent to the area of the damaged wall. The spool and stent are then advanced while the sheath is held stationary. This pushes the stent out the end of the sheath and releases the stent such that the roll unwinds and expands against the damaged vessel wall.

25 Claims, 1 Drawing Sheet

U.S. PATENT DOCUMENTS

| | | |
|---|---|---|
| 5,122,154 | 6/1992 | Rhodes . |
| 5,123,917 | 6/1992 | Lee . |
| 5,147,370 | 9/1992 | McNamara et al. . |
| 5,156,620 | 10/1992 | Pigott . |
| 5,167,614 | 12/1992 | Tessmann et al. . |
| 5,171,262 | 12/1992 | MacGregor . |
| 5,192,307 | 3/1993 | Wall . |
| 5,195,984 | 3/1993 | Schatz . |
| 5,211,654 | 5/1993 | Kaltenbach . |
| 5,211,658 | 5/1993 | Clouse . |
| 5,211,683 | 5/1993 | Maginot . |
| 5,219,355 | 6/1993 | Parodi et al. . |
| 5,234,448 | 8/1993 | Wholey et al. . |
| 5,242,399 | 9/1993 | Lau et al. . |
| 5,254,127 | 10/1993 | Wholey et al. . |
| 5,256,141 | 10/1993 | Gencheff et al. . |
| 5,256,764 | 10/1993 | Tang et al. . |
| 5,261,878 | 11/1993 | Galindo . |
| 5,266,073 | 11/1993 | Wall . |
| 5,269,802 | 12/1993 | Garber . |
| 5,274,074 | 12/1993 | Tang et al. . |
| 5,290,295 | 3/1994 | Querals et al. . |
| 5,306,294 | 4/1994 | Winston et al. . |
| 5,344,426 | 9/1994 | Lau et al. . |
| 5,354,309 | 10/1994 | Schnepp-Pesch et al. . |
| 5,372,600 | 12/1994 | Beyar et al. . |
| 5,405,379 | 4/1995 | Lane . |
| 5,411,551 | 5/1995 | Winston et al. . |
| 5,443,500 | 8/1995 | Sigwart . |
| 5,593,434 | 1/1997 | Williams ..... 623/12 |

STENT CONSTRUCTION OF ROLLED CONFIGURATION

Matter enclosed in heavy brackets [ ] appears in the original patent but forms no part of this reissue specification; matter printed in italics indicates the additions made by reissue.

FIELD OF THE INVENTION

This invention relates in general to the field of medical implants and more particularly to a stent which is constructed in an improved manner for simple and effective placement in a body passage to reinforce a damaged area.

BACKGROUND OF THE INVENTION

Tubular prostheses commonly known as stents have been used to reinforce and strengthen damaged blood vessels and other body passages. For example, the blood vessels can collapse, dilate, become partially occluded or otherwise damaged by disease or other causes. The presence of an aneurysm or stricture in the blood vessel often requires implantation of a stent to strengthen the vascular wall in the area of the damage. Other passages in the body can also sometimes benefit from stent implantation, including the esophagus, the trachea, the gastro intestinal tract, the bile duct, the ureter and the urethra.

The benefits or self-expanding stents have been recognized. A self-expanding stent is held in a contracted state until it has been positioned properly, typically with the aid of an instrument such as a catheter. After the stent has been placed properly in the damaged blood vessel, it is allowed to expand against the damaged vessel will in order to reinforce the damaged area. Examples or self-expanding stents are disclosed in Burton et al. U.S. Pat. Nos. 5,026,377 and 5,078,720, Hillstead U.S. Pat. No. 5,019,085, Wiktor U.S. Pat. No. 4,969,458 and Gianturco U.S. Pat. No. 5,041,126. The Wicktor and Gianturco stents are in the form of coiled or looped wires that are unable to contact the entirety of the weakened vessel wall. The same is true of the Hillstead stent which takes the form of a multiple loop wire structure. The stents disclosed in the two Burton patents are braided structures that are likewise incapable of contacting the entirety of the damaged vessel wall. All of the stents and particularly their placement means are complicated to construct, and the stents are difficult to place precisely in the damaged vessel.

SUMMARY OF THE INVENTION

The present invention is directed to an improved stent which is particularly characterized by a stronger construction, the ability to provide a solid and continuous wall that lines the entirety or the damaged part of passage wall in which it is implanted, and by ease and accuracy of placement. In accordance with the invention, a stent is provided in the form of a flexible metal sheet which is closely wound around a spool in a spiral roll. A sheath initially surrounds the roll in order to retain it in a contracted state. The spool, stent and sheath can be inserted together into the body with the spool following a guide wire until it is located adjacent to the damaged area. Then, the sheath is held stationary while the spool is pushed out the end of the sheath, with a flange on the spool making certain that the tightly coiled roll remains on the spool. Once the spool has cleared the sheath, the roll is released and allowed to expand against the damaged wall of the vessel. The sheath and spool can then be withdrawn, leaving the stent in place.

An alternative embodiment or the invention eliminates the sheath and instead holds the stent in its retracted state by means of a pair of control cords which are connected by slip knots to flanges on the spool located adjacent to the opposite ends of the stent. When the stent has been properly positioned, the cords can be pulled to release the slip knots and allow the stent to expand against the vessel wall. In both embodiments, multiple stents can be carried on the some spool if it is necessary to strengthen the vessel in more than one area.

Because the stent takes the form of a continuous sheet, the stent essentially contacts the entirety of the damaged vessel wall area, rather than simply reinforcing the damaged area as is the case with looped or coiled wires or braided netting type structures. In addition, the stent preferably has multiple layers that bear against one another when the stent is in its expanded condition. This further enhances the strength of the stent and provides multiple layers that are held against one another by friction resulting from the tendency for the stent to expand under the influence of internal spring force.

The method by which the stent is placed in the proper position and allowed to expand against the vessel wall is improved in a number of respects compared to what has been proposed in the past. The placement method is simple and accurate and does not involve complexities such as the need to inflate a balloon catheter or other mechanism.

DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figures 1, 2, 3, 4, 5, 6:
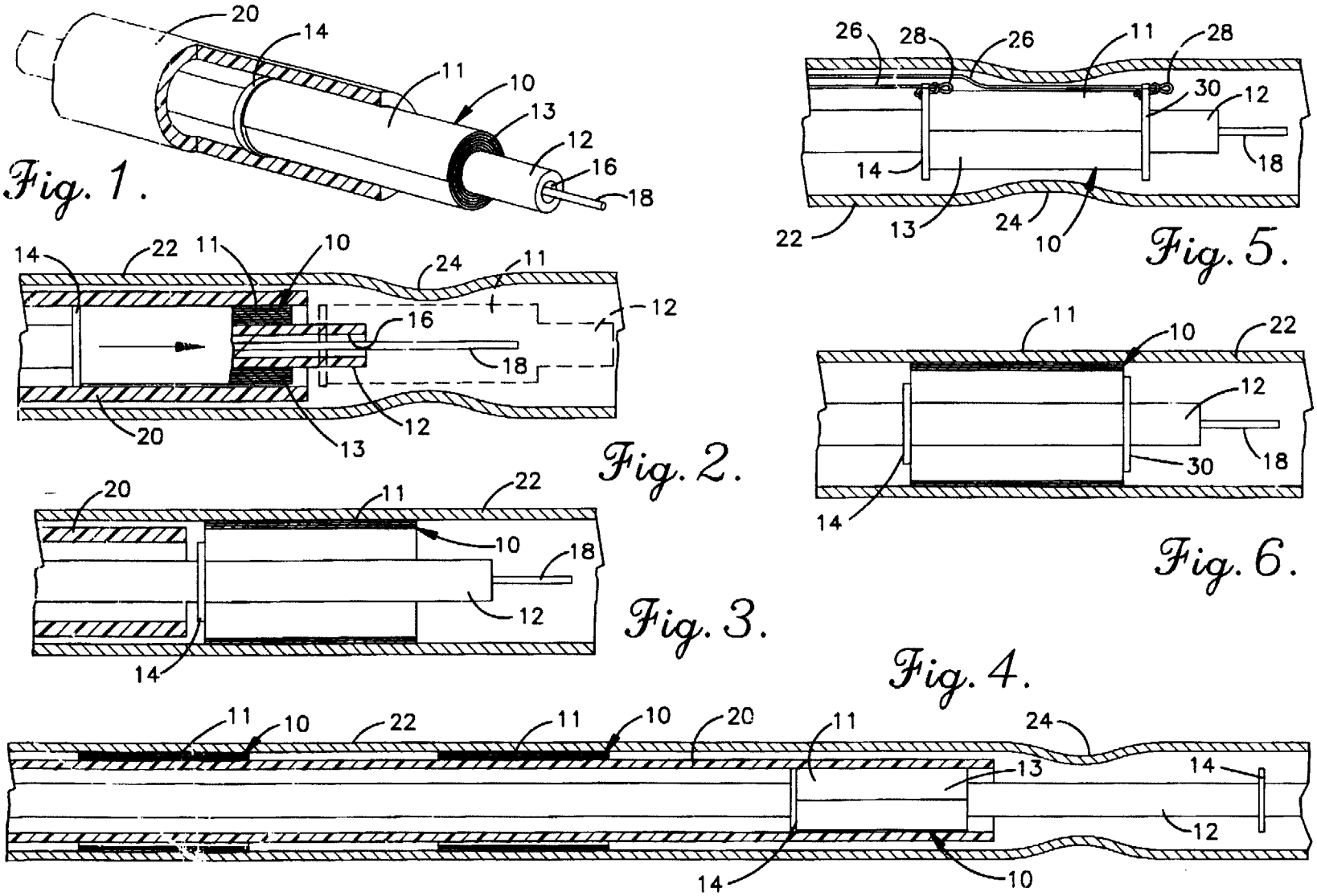
FIG. 1 is a fragmentary perspective view of a stent and placement system for the stent, all constructed according to a preferred embodiment of the present invention, with the stent in its retracted condition and part of the sheath shown in section for purposes of illustration.
FIG. 2 is a fragmentary sectional view illustrating the stent being applied to a stricture in a blood vessel, with the broken lines depicting the spool and stent pushed out the end of the sheath.
FIG. 3 is a fragmentary sectional view similar to FIG. 2, but showing the stent expanded against the damaged vessel wall prior to withdrawal of the sheath and spool.
FIG. 4 is a fragmentary sectional view showing an alternative embodiment of the invention in which the spool is constructed to carry multiple stents and to apply them to multiple damaged areas are blood vessel.
FIG. 5 is a fragmentary sectional view or a stent arrangement constructed according to an alternative embodiment of the invention, with the stent in is retracted condition and positioned properly for application to a damaged structure in a blood vessel.
FIG. 6 is a fragmentary sectional view similar to FIG. 5, but showing the stent released and expanded against the damaged vessel wall prior to withdrawal of the spool.

Referring now to the drawings in more detail and initially to FIG. 1 in particular, numeral 10 generally designates a stent which is constructed in accordance with a preferred embodiment of the present invention. The stent 10 takes the form of an initially flat metal sheet which is wound lightly around a core which is in the form of a tubular spool 12. The stent 10 is preferably constructed of a stainless steel foil which is commercially available under the trade designation PH15-7. Condition CH900. The thickness of the sheet 11 is preferably about 0.0005 inch. When the sheet 11 is coiled around the spool 12, it is in the shape of a spiral roll 13, and its outside diameter may be approximately 1.5 millimeter. The sheet 11 is long enough that there are approximately six or seven layers of the sheet which overlap one another when the roll 13 is in the contracted position in FIGS. 1 and 2. The roll presents a plurality of adjacent arcuate layers of the sheet in a direction transverse to the longitudinal axis of the core.

The sheet 11 produces an inherent spring force which tends to expand the sheet from the retracted condition of the roll 13. By way or example, it is contemplated that the sheet will initially be rolled to a diameter of approximately 5 millimeters and then heat treated in that condition in order to relax the internal stresses that arc induced by winding the sheet to a partially contracted condition. Following the heat treatment, the material can be rolled into the tighter roll 13 (approximately 1.5 millimeter in diameter), and the roll will have fewer internal stresses than if it were initially wound into the tight 1.5 millimeter cylinder. The internal spring force of the roll 13 will tend to cause it to unwind to an expanded condition in which its diameter is approximately 5 millimeters (the diameter at which the heat treatment takes place).

The sheet 11 is wound tightly on the spool 12 near one end of the spool, and one end of the roll 13 butts against a flange 14 which is formed on the spool 12 at a location spaced from the end of the spool. The flange 14 projects radially from the spool 12 and has a diameter approximately equal to the diameter of the stent 10 in its fully contracted condition. The flange 14 is spaced from the end of the spool a distance greater than the axial length of the stent 10. The spool 12 is provided with a central axial passage 16 which receives a guide wire 18. As will be explained more fully, the spool 12 can be moved along the guide wire 18 in order to properly position the stent 10.

The stent 10 is maintained in its fully contracted position by an elongated sheath 20 having a tubular shape. The sheath 20 has an inside diameter substantially equal to the outside diameter of the stent 10 in its fully retracted condition. The spool 12 and stent 10 are located within the sheath 20, with the outer surface of the stent 10 in contact with the inside surface of the sheath 20. The sheath 20 has a tubular form in order to receive the stent 10 and spool 12. The outside diameter of the sheath 20 is preferably somewhat smaller than the body passage in which the stent 10 is to be implanted. The spool 12 and sheath 20 are long enough that they can be advanced into a vessel to the area which is to be treated with the stent while the ends remain outside of the body.

In use, the sheath 20, with the stent 10 and spool 12 inside of it, is inserted into the body and advanced until its end is adjacent to an area of a body passage in which stent is to be implanted. For example, with reference to FIG. 2, the sheath 20 may be inserted through a blood vessel 22 until the leading end or the sheath is adjacent to the damaged area such as the structure 24. The advance of the sheath 20 is then stopped, and the tube 12 is advanced while the sheath 20 remains stationary. As the tube is thus pushed out through the end of the sheath 20, the spool carries the stent 10 with it because the flange 14 pushes the stent forwardly along with the spool. Once the flange 14 and the entirety of the stent 10 have cleared the end of the heath 20 in the position shown in broken lines in FIG. 2, there is no longer anything restraining the stent 10 against expansion. At this time, the stent is aligned with the structure 24.

Because the stent is no longer held against expansion, it expands naturally under the influence or its inherent spring force to the full diameter or the vessel 22. In the fully expanded condition of the stent shown in FIG. 3, its outside surface contacts the inside surface of the vessel wall and effects expansion of the structure 24.

It is noteworthy that the sheet construction of the stent 10 allows it to line the entirety of the damaged surface of the vessel 22 at the structure 24 and the adjacent areas of the vessel wall. In this manner, the stent is able to remove the occlusion in the vessel that is caused by the structure 24 and is also able to reinforce and strengthen the damaged vessel area at and near the structure 24. Normal circulation through the vessel is thus restored. Rather than holding the sheath 20 stationary and pushing the stent out through its end, the sheath can be advanced until the stent is aligned with the damaged area, and the sheath can then be retracted while the spool 12 and stent 10 are held stationary. When the sheath is withdrawn far enough to release the stent, the stent expands in the manner previously indicated.

In the fully expanded condition of the stent, there are preferably at least two overlapping layers which bear against one another over a substantial portion of their circumference of an inner layer and are held against one another by friction caused by the tendency of the stent to expand to its undeformed condition. These overlapping layers assure that the stent will be securely held in place and provide enhanced structural integrity by reason of the multiple layer structure that is implanted in the damaged area of the vessel. Once the stent has fully expanded, the sheath 20 and the tube 12 can be removed from the vessel, along with the guide wire 18. In its fully expanded condition, the diameter or the stent is at least as great as the inside diameter of the vessel so that when the stent expands into contact with the damaged vessel wall, it is held securely against the roll under the influence or its inherent spring force.

FIG. 4 depicts an arrangement which is for the most part identical to that shown in FIGS. 1–3. The principal difference is that the FIG. 4 construction has a spool 12 which is provided with a number of spaced apart stents 10 carried adjacent to different flanges 14. In use of the embodiment shown in FIG. 4, the stents 10 are applied in series to different weakened or damaged areas of the vessel 22, thereby strengthening the different damaged areas of the vessel to which the stents are applied. Virtually any desired number of stents can be carried on the spool 12.

FIGS. 5 and 6 depict an alternative embodiment of the invention In which the sheath 20 is not present. In place of the sheath, the function of holding the roll 13 in its contracted condition is performed by a pair of control cords 26. One of the control cords 26 is fitted through the flange 14 and is provided with a slip knot 28 which is formed adjacent to the flange and which bears against the outer layer or the stent 10 in a manner to prevent the stent from expanding. The other control cord 26 is extended through a second flange 30 which is spaced from flange 14 a distance slightly greater than the length of the stent 10. The ends or the cords 26 opposite the slip knots 28 remain outside the vessel.

In use of the embodiment shown in FIGS. 5 and 6, the spool 12 is extended into the vessel until the stent 10 is aligned with the structure 24. Then, the control cords 26 are pulled to release the slip knots 28, thereby releasing the stent 10 which then expands naturally under the influence of the internal spring force to which it is subjected. The stent expands to the fully expanded condition shown in FIG. 6 in which it expands the stricture 24 and eliminates the occlusion presented by the stricture. In addition, the stent 10 lines the vessel and strengthens and reinforces the damaged vessel wall in the area or the structure in the same manner indicated previously. Once the stent has been fully expanded, the spool 12 and guide wire 18 can be withdrawn from the vessel.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A stent assembly for placement in a body passage to reinforce a damaged wall in the passage, comprising:

an elongated core;

an elongated, flexible sheet arranged on said core in a multiple layer roll having expanded and contracted conditions and having a spring force so that said sheet is urged toward the expanded condition, said roll being tightly wound on the core in the contracted condition and presenting in the expanded condition a diameter at least equal to the diameter of the body passage.

said roll being spirally wound on said core and having a tendency to radially expand, said roll presenting a plurality of adjacent, arcuate layers of said sheet in a direction transverse to the longitudinal axis of said core;

releasable means for retaining said roll in the contracted condition on said core while the core is being inserted into the passage to the location of the damaged walls; and means for effecting release of said releasable means to permit the roll to expand against the damaged wall in the expanded condition of the roll, said roll in the expanded condition thereof having at least two overlapping layers which overlap and bear against one another over a substantial portion of the circumference of [a] *an* inner layer, said expanded roll adapted for securely contacting said damaged wall by virtue of said radial expansion tendency.

2. The stent assembly of claim 1, including a first flange on said core against which one end of said roll is engaged in the contracted condition.

3. The stent assembly of claim 2, including a second flange on said core, said roll being retained between the first flange and said second flange in the contracted condition.

4. The stent assembly of claim 3, wherein said releasable means comprises a pair of control cords having slip knot connections with the respective first and second flanges arranged in a manner to retain the roll in the contracted condition, said slip knot connections being releasable upon pulling of said control cords to thereby release said roll for expansion thereof to the expanded condition.

5. The stent assembly of claim 4, wherein said core comprises a tubular spool having an axial passage therethrough for receiving a guide wire along which the spool may be guided to the location of the damaged wall.

6. The stent assembly of claim 1, wherein said core comprises a tubular spool having an axial passage therethrough for receiving a guide wire along which the spool may be guided to the location of the damaged wall.

7. The stent assembly of claim 1, wherein said sheet is constructed or a metal foil.

8. The stent assembly of claim 1, wherein said sheet is constructed or a stainless steel foil.

9. The stent assembly of claim 1, wherein said releasable means comprises a sheath closely sleeved on said roll, said sheath being movable axially relative to said core to release from the roll.

10. The stent assembly of claim 1, including:

a second flexible sheet arranged on said core in a second multiple layer roll spaced from the first mentioned roll, said second roll having a contracted condition wherein the second roll is tightly wound on the core and an expanded condition wherein the second roll presents a diameter substantially equal to the diameter of the body passage, said second roll being urged toward the expanded condition;

releasable means for retaining said second roll in the contracted condition; and means for effecting release of the releasable means for said second roll.

11. The stent assembly of claim 10, wherein the releasable means for the first and second rolls comprises a sheath closely sleeved on the first and second rolls said sheath being movable axially relative to said core to release from the first and second rolls in succession.

12. Apparatus for reinforcing a damaged wall of a body passage, comprising:

an elongated core;

an elongated stent in the form of a flexible sheet spirally wound around the core in a multiple layer roll having contracted and expanded conditions, said sheet being wound tightly on the core in the contracted condition and having a spring force which tends to radially expand toward the expanded condition thereof wherein the sheet assumes a size to contact the damaged wall, and said roll [presenting] *having* a plurality of adjacent, arcuate layers [of said sheet in a direction transverse top the longitudinal axis of the core];

a sheath fitting closely around said roll to hold the sheet in the contracted condition, said sheet being movable axially relative to the roll to permit the sheath to release from the roll and thereby allow expansion of the sheet against the damaged wall in the expanded condition, said roll in the expanded condition thereof having at least two overlapping layers, which overlap and bear against one another over a substantial portion of the circumference of the inner layer, said expanded roll adapted for securely contracting said damaged wall by virtue of said radial expansion tendency of the roll.

13. Apparatus as set forth in claim 12, including a flange on said core against which one end of said roll is engaged in the contracted condition.

14. Apparatus as set forth in claim 12, wherein said core comprises a spool having an axial passage therethrough for receiving a guide wire along which the spool may be guided to the location of the damaged wall.

15. Apparatus as set forth in claim 12, wherein said sheet is constructed of a thin metal foil.

16. Apparatus as set forth in claim 12, wherein said sheet is constructed of a thin stainless steel foil.

17. Apparatus as set forth in claim 12, including second stent in the form of a second flexible sheet wound around said core in a second multiple layer roll having contracted and expanded conditions, said second sheet being wound tightly on the core in the contracted condition and being biased toward the expanded condition wherein said second sheet assumes a size to contact the passage wall, said sheath fitting closely on the second roll to hold the second sheet in the contracted condition and being movable axially to release from the second roll and thereby allow the second roll to expand against the wall in the expanded condition.

*18. A stent for placement in a body passage to support a stricture or reinforce a damaged wall in the passage, comprising:*

*an elongated flexible sheet arranged in a multiple layer roll having expanded and contracted conditions and having a spring force, so that when said sheet is in said contracted condition, said spring force urges said sheet to expand toward the expanded condition, said roll presenting in the expanded condition a diameter at least equal to the diameter of the body passage;*

*said roll presenting in its contracted condition a plurality of adjacent, arcuate layers;*

*said roll being retained in the contracted condition during an insertion into said passage to the location of said damaged wall by a retaining structure adapted to be inserted into said body passage;*

*wherein upon release of said roll from said retaining structure at the location of said damaged wall, said spring force urges expansion of said roll into the expanded condition such that said roll contacts said damaged wall, said roll further having in the expanded condition a plurality of overlapping layers which overlap and bear against one another over a substantial portion of the circumference of an inner layer, said expanded roll further having sufficient structural integrity to effect reinforcement or support of said damaged wall.*

*19. The stent assembly of claim 18, wherein said sheet is constructed of a metal foil.*

*20. The stent assembly of claim 19, wherein said metal foil is stainless steel.*

*21. The stent assembly of claim 19, wherein prior to insertion into the body passage, said metal foil roll has been heat treated while in said expanded condition to reduce internal stresses within said roll.*

*22. The stent assembly of claim 18, wherein in said contracted condition, said roll has approximately, six or seven adjacent arcuate layers of said sheet.*

*23. The stent assembly of claim 18, wherein said retaining structure comprises a sheath which closely overlaps said roll in its contracted condition, said sheath being movable axially with respect to said roll to effect ejection of said roll from said sheath.*

*24. The stent assembly of claim 23, further comprising a flange slidably disposed within said overlapping sheath at a point proximal to said roll, said flange being adapted to provide a force on said roll to eject it from said sheath at a desired location within the body.*

*25. A stent assembly for placement in a body vessel for treatment of a vessel abnormality, the stent assembly comprising:*

*a flexible sheet arranged in a multiple layer roll having expanded and contracted conditions and having a spring force, so that when said sheet is in said contracted condition, said spring force urges said sheet to expand toward the expanded condition, said roll presenting in the expanded condition a diameter at least equal to the full diameter of the vessel;*

*said roll presenting in the contracted condition a plurality of adjacent, arcuate layers;*

*wherein when said contracted roll is introduced within said vessel at or near said abnormality and is not constrained so as to be maintained in its contracted condition said spring force will urge said stent into said expanded condition, said expanded condition having multiple layers of said sheet that bear against one another over a substantial portion of the circumference of an inner layer, said multiple layers having a frictional force which resists stent contraction thereby enhancing the structural integrity of said stent such that said stent is able to firmly contact the vessel wall to effect treatment of said abnormality.*

* * * * *